(12) United States Patent
Asokan et al.

(10) Patent No.: US 7,931,813 B2
(45) Date of Patent: Apr. 26, 2011

(54) PROCESS FOR THE REDUCTION OF BIOFOULING USING ELECTRIC FIELDS

(75) Inventors: Thangavelu Asokan, Bangalore (IN); Setu Chokshi, Lawrenceville, NJ (US); Yuseph Montasser, Alberta (CA); David M. Polizzotti, Yardley, PA (US); Yatin Tayalia, Bangalore (IN)

(73) Assignee: General Electric Company, Schenectady, NY (US)

( * ) Notice: Subject to any disclaimer, the term of this patent is extended or adjusted under 35 U.S.C. 154(b) by 17 days.

(21) Appl. No.: 11/956,561

(22) Filed: Dec. 14, 2007

(65) Prior Publication Data

US 2009/0152207 A1 Jun. 18, 2009

(51) Int. Cl.
*C02F 1/469* (2006.01)
(52) U.S. Cl. .............. 210/748.01; 205/740; 205/722; 210/760; 210/600
(58) Field of Classification Search ............ 205/740, 205/722; 210/748, 760, 600
See application file for complete search history.

(56) References Cited

U.S. PATENT DOCUMENTS

| 5,048,404 | A | 9/1991 | Bushnell | |
|---|---|---|---|---|
| 6,277,288 | B1 * | 8/2001 | Gargas | 210/748 |
| 6,755,977 | B2 * | 6/2004 | Brunsell | 210/648 |
| 2002/0056634 | A1 * | 5/2002 | Pitts et al. | 204/164 |
| 2004/0112762 | A1 * | 6/2004 | Wilms et al. | 205/727 |
| 2004/0238453 | A1 | 12/2004 | Cho | |
| 2005/0211638 | A1 * | 9/2005 | Schrive et al. | 210/748 |
| 2005/0230312 | A1 | 10/2005 | Chancellor | |
| 2006/0118485 | A1 * | 6/2006 | Gallagher et al. | 210/609 |
| 2006/0290014 | A1 | 12/2006 | Swoboda et al. | |
| 2007/0074975 | A1 * | 4/2007 | Buschmann et al. | 205/466 |
| 2007/0131556 | A1 | 6/2007 | Lambie | |

FOREIGN PATENT DOCUMENTS

| EP | 1736442 A | 12/2006 |
|---|---|---|
| WO | 0248053 | 6/2002 |
| WO | 2004063098 A2 | 7/2004 |

OTHER PUBLICATIONS

Romo Rodrigo, F.V. Pitts, M. Michael, PhD., Hector, Melvin G., MD "Composite Fouling Control in RO Membranes with High Voltage Capacitance-Based Technology" Apr. 23-24, 2002, Ultrapure Water 2002, Orlando Florida.

Hass, C. N. and Aturaliye, D. "Semi-quantitative characterization of electroporation-assisted disinfection processes for inactivation of Giardia and Cryptosporidium", Journal of Applied Microbiology, 1999, 86, 899-905.

(Continued)

*Primary Examiner* — Walter D Griffin
*Assistant Examiner* — Cameron J Allen
(74) *Attorney, Agent, or Firm* — GE Global Patent Operations; Peter T. DiMauro

(57) ABSTRACT

A process to reduce or prevent biofouling, by destroying or deactivating microbiological content of feedwater, or other liquid, prior to its entrance into membranes or process equipment, such as heat transfer equipment. The process comprises the use of electrical discharge and/or electric fields to destroy microbes that result in the biofouling of surfaces. By destroying the microbiological content of the water the microbiology no longer is able to create a restricting biofilm upon or within said process equipment.

7 Claims, 1 Drawing Sheet

OTHER PUBLICATIONS

Haas, Charles N., and Aturaliye, Dhumal, N. "Kinetics of Electroporation-Assisted Chlorination of Giardia Muris" Wat. Res. vol. 33, No. 8 pp. 1761-1766, 1999 © 1999 Elsevier Science Ltd.
International Search Report issued in connection with corresponding Application No. PCT/US2008/080302 on Jun. 2, 2009.

H. Bluhm, W. Frey, C. Gusbeth, M. Sack, C. Schultheiss: "Aufschluss und Abtötung biologischer Zellen mit Hilfe starker gepulster elektrischer Felder". Nachrichten-Forschungszentrum Karlsruhe, vol. 35, No. 3, pp. 105-110 (2003).

* cited by examiner

PROCESS FOR THE REDUCTION OF BIOFOULING USING ELECTRIC FIELDS

BACKGROUND OF THE INVENTION

1. Field of the Invention

The present invention relates to a process t for addressing the problems associated with microbial fouling of surfaces. Of particular interest in this regard is microbial fouling of membrane and heat transfer surfaces.

2. Description of the Related Art

Clean water is often required in many industries, such as the chemical, food and beverage, pharmaceutical, electronics, and power industries. Typically, applications in these industries require treatment of a water source to remove contaminants. Various techniques and chemistries for water treatment are known, including distillation, filtration, ion exchange, reverse osmosis, photo oxidation, and ozonation either alone or in combination with traditional chemical clarification. In many instances, feedwaters containing numerous dissolved solids, organic moieties, and microbially active components will move through a water treatment system or equipment such as a heat exchanger and thereby create a fouling condition that compromises efficiency of said system or equipment.

Membranes are commonly used to remove contaminants contained in process feedwater. Membranes of interest include microfilters, nanofilters, ultrafilters and reverse osmosis membranes. One problem that arises as a natural consequence of the filtration operation is the fouling of membrane surfaces. The fouling material can be broken down into the general classifications of organics, (i.e. humic substances, fats, oils and grease), inorganic, (i.e. clay, silt, calcium carbonate and calcium phosphate), and microbiological. The last group of contaminants (i.e. microbiological) is those to which the currently claimed process is applied.

Chemicals are commonly used to prevent the deposition of contaminants within the membrane. For example, antiscalants are used to remediate inorganic fouling. However, antiscalants have little or no effect on microbial fouling. To control microbial fouling, biocides are often used. However, while biocides kill microorganisms, some microorganisms still exist within the membrane, may feed off the residues of killed organisms and their presence act as a resistance to flow and therefore impede the efficient operation of the membrane system. Exacerbating the situation is the fact that the resultant biofilm that forms on the membrane may provide a protective niche for bio-growth and is difficult to remove. Normal treatments to remove or clean the membrane of microbial contamination requiring the use of chemicals can negatively impact the life of the membrane.

Indeed, the presence of a biofilm not only presents resistance to fluid flow, but when deposited on the surfaces of equipment, such as heat transfer equipment (e.g. heat exchangers used in industrial cooling towers) the biofilm presents a resistance to heat transfer. As in the case of membranes, chemicals known as biocides can be used to alleviate the problem, however these chemicals are costly and represent an environmental hazard. Additionally, the dead microbial materials that remain also hinder heat transfer efficiency. Hence there is a need to remediate biofouling on equipment such as heat transfer surfaces in industrial water processes For instance in a cooling tower the effect of accumulated biomass on the surfaces of the heat transfer equipment is similar to that accumulated on membranes. In one case, a fluid flow restriction results, while in the other a heat transfer flow restriction is the result. In either case, there is a need for a way to prevent microorganisms from entering the equipment, growing and propagating into established biofilms. The presently claimed process addresses this problem by mitigating the effect of microbial matter before it can interact with internal membrane and/or heat transfer surfaces.

SUMMARY OF THE INVENTION

A process has been found to prevent biofouling, by using electrical discharge and/or electric fields to destroy microbes that result in the biofouling of surfaces. In particular, the process calls for destroying the microbiological content of the feedwater or other liquid stream, prior to being subjected to other processes, such as membrane filtration or circulation through a heat exchanger. By destroying or denaturing the microbiological content of the water the microbiology no longer is able to create a restricting biofilm upon or within said process equipment.

In particular, in one embodiment of the invention, feedwater is treated with a device capable of generating strong electrical fields of the order of from about 10 to about 80 Kv/cm that are capable of destroying microbial cells contained in the feed water. The system essentially sterilizes the water and effectively removes viable or viability sustaining microbiological matter by perforating cells via electric field effects.

Another embodiment of the invention relates to a method that involves repeated, and rapid capacitive electrical discharge. The effect of the capacitive electrical discharge is to kill the biological contamination in much the same way as previously described.

A further embodiment provides for the combination of either of the above embodiments in combination with chemical treatment. By subjecting the microbiological cells to electrical fields coupled with chemical treatment, it is possible to either reduce lethal field strength, and/or lower chemical dose rates and/or reduce overall treatment time to render a feedwater free of microbial contamination.

A further embodiment involves the remediation of microbial matter and/or recalcitrant organic moieties by combining chemicals capable of generating free radicals under the influence of either a corona discharge known as a Trichel pulse or UV light. In the case of the corona discharge, the electric field strength required to create the corona is a function of the diameter of the wire connected to the power supply. Typically, corona discharge can be initiated at potentials of 25 Kv and only a few milliamps on wires with diameters of only a few millimeters. In the case where the wire is a hollow conducting tube, it would be possible to introduce (via a pump) a chemical that would travel down the length of the hollow conducting tube, and as it exits from the tube, be subjected to ionizing radiation produced by the Trichel pulse that occurs at the opening of the hollow conducting tube by virtue of the high radius of curvature at the point where the chemical(s) would exit. By chemicals I mean either liquids or gases that on ionization generate many free radicals that are then available to scavenge microbial matter and/or recalcitrant organic materials. In one embodiment, a grid of such wires might be used so as to give good cross sectional area coverage in a flowing pipe or other means so that the beneficial effects of the corona discharge may be optimized. The polarity of the corona discharge is not necessarily important, however, a benefit of using a corona with electric power that is negative with respect to ground is that one by-product is ozone. Ozone is a known disinfectant and is prone to generating the kinds of radicals that could be of value for the intended purpose.

What has been said for corona discharge is equally applicable to UV radiation. In this case, the opportunity of having the chemistry travel through or around a UV fiber optic or some other contrivance that efficiently conveys UV radiation to a location where it can interact with chemistry to create free radicals (e.g. via photochemical reactions) in flowing water which would then be capable of interacting with microbial matter and/or recalcitrant organic moieties.

In either case, the end game is the generation via electrical or UV or other energy device a source of free radicals from organic moieties that would otherwise not generate such free radicals and to have these radicals interact with undesirable components in the water. The short-lived nature of free radicals makes them ideal for the purpose.

The various features of novelty that characterize the invention are pointed out with particularity in the claims annexed to and forming a part of this disclosure. Changes to and substitutions of the various components of the invention can of course be made. The invention resides as well in sub-combinations and sub-systems of the elements described, and in methods of using them.

BRIEF DESCRIPTION OF THE DRAWINGS

Refer now to the figures, which are meant to be exemplary and not limiting, and wherein like elements are numbered alike, and not all numbers are repeated in every figure for clarity of the illustration.

DETAILED DESCRIPTION OF THE INVENTION

Figure 1:
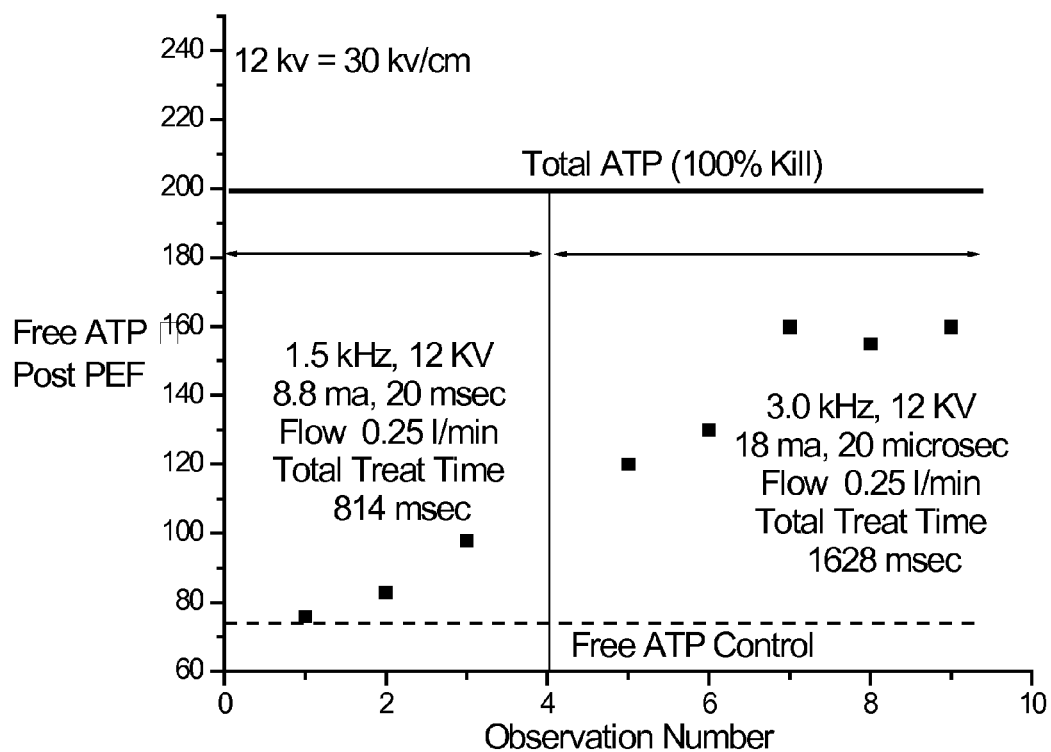
FIG. 1 is an illustration of a typical set of tests using ATP as a measure of effectiveness.

Approximating language, as used herein throughout the specification and claims, may be applied to modify any quantitative representation that could permissibly vary without resulting in a change in the basic function to which it is related. Accordingly, a value modified by a term or terms, such as "about", is not limited to the precise value specified. In at least some instances, the approximating language may correspond to the precision of an instrument for measuring the value. Range limitations may be combined and/or interchanged, and such ranges are identified and include all the sub-ranges included herein unless context or language indicates otherwise. Other than in the operating examples or where otherwise indicated, all numbers or expressions referring to quantities of ingredients, reaction conditions and the like, used in the specification and the claims, are to be understood as modified in all instances by the term "about".

As used herein, the terms "comprises," "comprising," "includes," "including," "has," "having" or any other variation thereof, are intended to cover a non-exclusive inclusion. For example, a process, method, article or apparatus that comprises a list of elements is not necessarily limited to only those elements, but may include other elements not expressly listed or inherent to such process, method article or apparatus.

The present invention is directed to a process for preventing or minimizing the biofouling of industrial process equipment such as membranes and cooling tower equipment. The microbiological content of the feedwater, or other liquid, is subjected to a high electric field or a rapid electrical capacitive discharge either of which is used alone or in combination with chemistry that destroys the cells, and therefore results in little to no biofouling of the process equipment.

In one embodiment of the present invention, a high voltage process using pulsed electric fields is applied to the water or other liquid prior to the time it enters the process equipment. The pulsed electric field works by using a series of short, high voltage pulses, to create high electric fields that perforate cell walls. By "perforate" is meant that the electrical field is sufficiently high to induce electroporation, opening channels that effectively expose the interior of the organism to the destructive field and/or surrounding medium. By damaging or destroying the cell walls, the microbiological content of the water is destroyed, and there is no longer any living microbial matter to cause biofouling of the process equipment. Specifically, without being tied to a specific mechanism of operation, applicant believes that the described electrical treatment kills the organism and/or denatures much of its biological material. In accordance with a principal aspect of the invention, the application of the electric fields takes place prior to the water entering the equipment or membrane, such that the application of the electric field can be considered a pretreatment process.

A preferred field strength for the electric field to be used for the intended purpose is between about 10 to about 80 KV/cm, and is preferably about 25 to 60 KV/cm. The pulses can be composed of any shape, and can be chosen based on how much power is required for a particular application. In one application a pulse that may be applied as a square wave will have a duration of between about $10^{-4}$ to about $10^{-9}$ sec with about $10^{-6}$ sec being an optimal duration. A pulse rate, e.g., a pulse repetition frequency, is to be chosen on the basis of the flow rate of water to be treated such that no portion of the water is left untreated by the pulsing circuit. Typically such pulse rates will be of the order of from about 2 and about 5 KHz with a preferred rate of 3 KHz.

In still another embodiment, it is possible to achieve essentially the same microbial deactivation as described above, using what is known in the art as a "lightning discharge". In this embodiment, a capacitive discharge is directed through the water to be treated. Water passing through the "lightning discharge zone" is disinfected. The essential elements of this embodiment include electrical discharges using microsecond pulses with consequent generation of oxidizing radicals, shock waves and UV. To further enhance the effectiveness of this technique, air or gas bubbles may be introduced into the water. The bubbles essentially cause cavitation at the time of discharge causing local temperature and shock waves that augment oxidizing radicals and UV radiation along the main discharge path. The rise time of the pulse can vary from microseconds to a few milliseconds depending upon the flow of water to be treated and the level of microbial contamination. In operation, this embodiment may consist of one or more of the following: (i) one or both electrode tips may be located at the air/water interface or at the surface of the water column; (ii) the electrode surface may be covered by a dielectric or insulation keeping only a small portion of the tip exposed to water, thus providing a high-current density or high field gradient region for initiation of the discharge; (iii) enhancing the quantity of the oxidizing radicals by introducing air or gas bubbles or other chemistry capable of interacting with the capacitive discharge to create such free radicals (where the air or gas bubbles may also decrease the bulk conductivity of the water to allow the charging circuit to attain a higher breakdown voltage without leakage occurring before the onset of discharge, cavitation and ensuing radical formation); and/or (iv) injecting air and/or chemistry through the tip of the high voltage or grounded electrodes or both. A further refinement of this technique is the use of magnetic fields to confine the discharge to eliminate so called "treeing" discharges, so that the current paths follow a compact, space-filling bundle, such as a dense columnar bundle.

One factor that plays an important role in the shape of the pulse and the energy consumed in the lightning discharge process is the conductivity of the liquid medium. For example the range of conductivities may range from 13 to 15 μS/cm for deionized water to about 1.2 to 1.5 mS/cm for tap water. The higher conductivity can greatly impact the efficacy of the treatment process. The process can be broken down into the pre-breakdown region and the post-breakdown region. The magnitude of the current which occurs during the pre-breakdown region is highly dependent on the conductivity of the liquid. The pre-breakdown current, which can be as much as 60 times that of the post-breakdown current, does not contribute anything to the treatment process and as a result to maximize the efficiency, it should be minimized. The pre-breakdown current can be limited by limiting the conductivity of the medium or by modifying the discharge characteristics so that the breakdown occurs right after the peak, making the pre-breakdown current insignificant. For example, drive circuitry that allows an essentially vertical leading edge, e.g., a microsecond or nanosecond rise time, can achieve breakdown voltage despite the aqueous conductivity, or the conductivity of the water may be lower by providing microbubbles to disrupt the pre-breakdown leakage current paths.

The number of pulses applied to the water medium also impacts the conductivity and water temperature. As the number of "shots" or pulses applied increase the conductivity in the vessel increases. This factor may be attributed to the fact that during the discharge some of the metal on the surface of the electrode is vaporized and then dissolved into the water as an ion, or may be attributed to the formation of partially ionized regions or pathways that the form a path of least resistance for the next discharge.

Another factor to consider is the effect of the gap distance on the process. Increasing the gap voltage increases the magnitude of the voltage that has to be applied to obtain the required high voltage breakdown condition. Increasing the voltage also increases the amount of energy delivered by the impulse simple due to the fact that more energy will be stored in the capacitors during charging to the higher voltage.

In an alternate embodiment, both the pulsed electric field and the "lightning discharge" methods described above may be used with sub lethal strength such that microbes are inactivated long enough so that they may travel through the process equipment without colonizing and creating biofilm. This effect may be described as a 'stun' effect, in that the microbes and their metabolic or enzymatic processes are apparently interrupted, denatured or stunned at least for a time. Indeed this process may be enhanced by the addition of sub lethal doses of chemicals. In this embodiment advantage is taken of the fact that while microbial cells are perforated by electric field effects, the cells so affected are rendered more susceptible to lower, and normally sub lethal, doses of chemical agents. Incorporation of these agents may either further inactivate and/or kill the microbes contained in the water. Exemplary chemical agents that may be used in this way include, but are not limited to biocides and/or disinfectants or oxidizers commonly known to those skilled in the art. For example, disinfectants may include chlorine, hydrogen peroxide, potassium permanganate and combinations thereof. The biocides or disinfectants may be present prior to or subsequent to the pulse being discharged.

The process according to the present invention can be utilized in a variety of systems, including but not limited to aqueous systems, and food and beverage processing. It is particularly applicable in those systems that include membranes, to prevent the biofouling of said membranes, microfiltration, nanofiltration, and reverse osmosis membranes. Examples of aqueous systems in which the process can be applied, but not limited to, are open recirculating cooling water systems, pulping and papermaking systems, water transport pipelines, closed cooling systems, reverse osmosis systems, air washer systems, shower water systems, once through water systems, hydrocarbon storage systems, hydrocarbon transport pipelines, metalworking fluid systems, and aqueous mineral processing systems. The cost and effectiveness of the present process may be particularly advantageous in certain situations, such as the polish loop of a UPW plant where low conductivity of the water and the low level of biomaterial allows a relatively straightforward electrical implementation and highly effective treatment efficiency.

While the present invention has been described with reference to preferred embodiments, various changes or substitutions may be made on these embodiments by those ordinarily skilled in the art pertinent to the present invention without departing from the technical scope of the present invention. Therefore, the technical scope of the present invention encompasses not only those embodiments described above, but also all that fall within the scope of the appended claims.

EXAMPLES

The following is an example of the effectiveness of the pulsed power systems described in this invention.

To test the efficacy of the inventive method, a series of tests were completed using ATP (Adeninetriphosphate). Two ATP tests were made. In the first, a "free" or "background" ATP measurement is made before and after subjecting the sample to a pulsed electric field (PEF) cell. In this way, the increase in "free" ATP affected by the PEF cell is determined. A second ATP test is made to determine the "total" ATP in the sample. By comparing post PEF treated ATP values to the total entitlement value, one can deduce the fraction of the total entitlement achieved by PEF treatment. When total and free ATP measurements are equal, all the cells in the sample have been lysed.

In some cases, plate count data was obtained, but there was usually a discrepancy between results obtained via ATP and the plate counts. The reason(s) for the differences are unclear, but may be related to "transient effects" Vs "total kill" (especially when field strengths are lower than optimal). Specifically, transient effects may inactivate microorganisms via injury (much like a Taser gun temporarily inactivates a human), but under long-term incubation (i.e. two days for plate counts) the organisms may recuperate or regenerate (again, like a Taser gun, after an inactivation period, the effects wear off). Hence one may observe a change in ATP value that is not "consistent" with a plate count result.

A typical set of tests using ATP as a measure of effectiveness is shown in FIG. 1. In this case, the field strength was 30 kv/cm, pulse frequency was varied from 1.5 to 3.0 kHz, pulse width was 20 usec and total treatment time varied from 814 to 1628 usec.

Based on ATP data, PEF treatment increased free ATP under the specified conditions. Also shown in FIG. 1 is the importance of treatment time. At 30 kv/cm, free ATP values were relatively low at a treatment time of 814 usec. However, increasing the treatment time from 814 to 1628 usec by increasing the repetition frequency from 1.5 to 3.0 kHz at the same flow rate, significantly increased the level of "free" ATP in the sample compared to the entitlement line (representing 100% kill). The entitlement line was not achieved in this test because electric field strength was not high enough to perforate all the cells (initial loading of the microorganism was of the order of $10^6$ cfu/ml).

Figure 2:
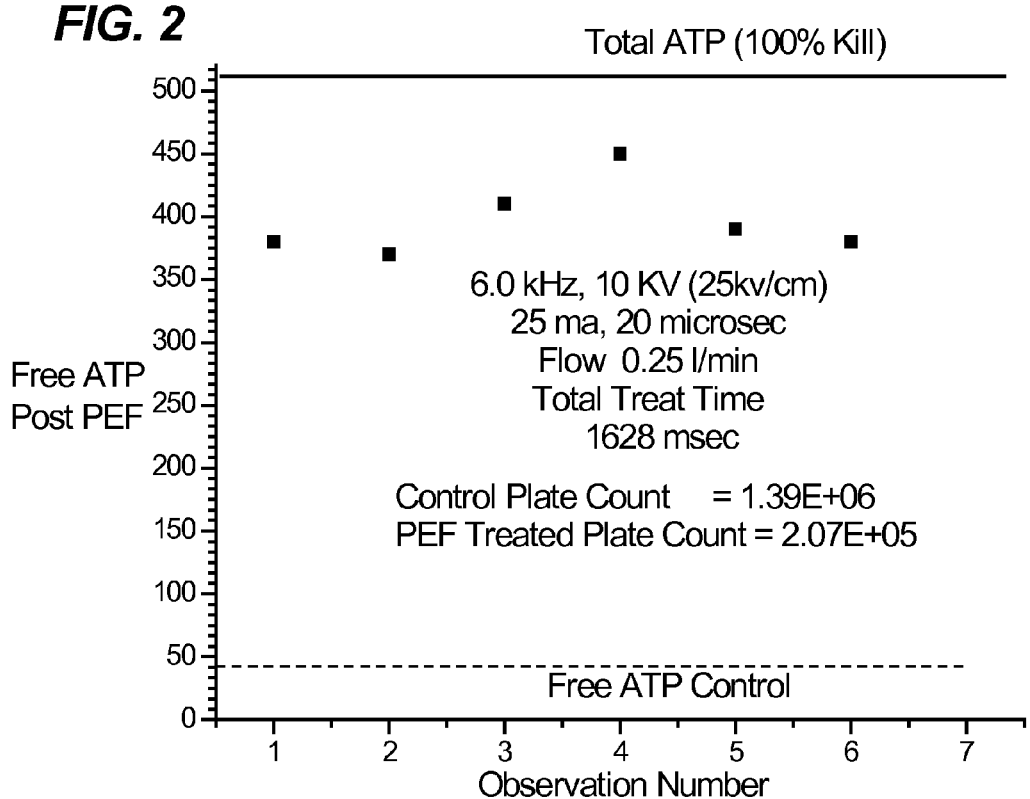
FIG. 2 is an illustration of the set of tests in FIG. 1 wherein plate counts were used to verify efficacy.

As shown in FIG. 2, the process was repeated, but this time plate counts, indicative of the concentration of remaining viable organisms, were used to verify efficacy.

In this case, a field strength of 25 Kv/cm was used due to equipment related issues. As noted, total kill was not achieved, but plate count data was favorable (e.g. control plate count was 1,390,000 colony forming units/ml. Treated (i.e. with the PEF unit operating) the number of colony forming units/ml decreased to approximately 207,000. (~85% reduction in colony forming units/ml)). While this plate count data was reasonably in line with the ATP assay results reported above, it is noted that there are other experiments not reported here where ATP data would suggest kill or some temporal effect, but plate count data failed to verify the effect. This may be due to the fact that plate count data is long term (2 day) indicator and does little to capture transient effects. However, the data suggests that if there is a stun effect of transient duration, such treatment would be quite efficacious for treating the feed water in a unit having a short residence time, such as a cross-flow filter of RO type or submicron pore size.

A final test set was conducted to verify, via plate count, that a field strength of at least 35 kV/cm would kill the organisms. The results of this test indicated that at this field strength, plate count values decreased from $10^5$ CFU/ml to $<10^2$ CFU/ml.

In the case of disinfection via lightning discharge, 100 ml of water containing pseudomonas and sulfur reducing bacteria were treated by a 10 Kv, 1.2 microsecond pulse. The energy used was of the order of 1.3 J/ml. Qualitative analysis of the treated water samples indicated that there were no detectable bacteria after 1 pulse.

We claim:

1. A process for the reduction of biofouling on surfaces of process equipment in an industrial aqueous system, comprising pretreating the water by subjecting the water to electrical discharges comprised of microsecond or sub-microsecond pulses to destroy or deactivate microbial matter by perforating cells, wherein said surfaces of process equipment comprises at least one of: surface of water filtration membrane and heat transfer surface, the process further comprising the introduction of air or gas bubbles in the water, wherein the air or gas bubbles are injected through the tip of electrodes.

2. The process according to claim 1 wherein one or more electrode tips may be located at the air/water interface, or at the surface of a water column.

3. The process according to claim 2 wherein an electrode surface may be covered by a dielectric or insulation so that only a small portion of the electrode tip is exposed to the water.

4. The process of claim 1 wherein the process is applied to potentiate activity of a biocide, that further comprises the addition of biocides, disinfectants or combinations thereof to the water subsequent to the electrical discharge process but prior to entering process equipment.

5. The process of claim 1, wherein the industrial aqueous system has a characteristic residence or transit time, and the process is effective to deactivate or stun viable biomaterial for said characteristic residence or transit time.

6. The process according to claim 1, wherein water filtration membrane comprises microfilter, nanofilter, ultrafilter, or reverse osmosis membrane.

7. The process according to claim 1, wherein said industrial aqueous system comprises open recirculating cooling water system, pulping and papermaking system, water transport pipeline, closed cooling system, reverse osmosis system, air washer system, shower water system, once-through water system, hydrocarbon storage system, hydrocarbon transport pipeline, metalworking fluid system, or aqueous mineral processing system.

* * * * *